US00PP15390P2

(12) United States Plant Patent
Arita

(10) Patent No.: US PP15,390 P2
(45) Date of Patent: Nov. 30, 2004

(54) ***COLEUS* PLANT NAMED 'KAKEGAWA CE8'**

(50) Latin Name: *Coleus×hybridus*
Varietal Denomination: Kakegawa CE8

(75) Inventor: Yo Arita, San Jose (CR)

(73) Assignee: Sakata Seed Corp., Yokohama (JP)

( * ) Notice: Subject to any disclaimer, the term of this patent is extended or adjusted under 35 U.S.C. 154(b) by 0 days.

(21) Appl. No.: 10/753,806

(22) Filed: Jan. 8, 2004

(51) Int. Cl.[7] ..... A01H 5/00
(52) U.S. Cl. ..... Plt./373
(58) Field of Search ..... Plt./373

(56) References Cited

U.S. PATENT DOCUMENTS

PP3,700 P * 4/1975 Datello ..... Plt./373

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Coleus* plant named 'Kakegawa CE8', characterized by its low and outwardly spreading plant habit; freely branching and vigorous growth habit; strong lateral branches; and green and dark purple bi-colored leaves with dark purple-colored venation and purple-colored petioles.

1 Drawing Sheet

Botanical classification/cultivar designation: *Coleus×hybridus* cultivar Kakegawa CE8.

BACKGROUND OF THE INVENTION

The present Invention relates to a new and distinct cultivar of *Coleus* plant, botanically known as *Coleus×hybridus*, and hereinafter referred to by the cultivar name Kakegawa CE8.

The new cultivar is the product of a planned breeding program conducted by the Inventor in Cartago, Costa Rica. The objective of the breeding program is to create new *Coleus* cultivars with a low spreading plant habit. The new *Coleus* was discovered and selected by the Inventor as a single seedling resulting from a self-pollination of a proprietary selection of *Coleus×hybridus* identified as code number 9CL-1, not patented. The new *Coleus* was discovered and selected from within the seedling progeny from the stated self-pollination in a controlled environment in Cartago, Costa Rica in 2000. This seedling was selected on the basis of its low and outwardly spreading plant habit and unique leaf coloration.

Asexual reproduction of the new cultivar by terminal cuttings taken in Salinas, Calif. since 2000, has shown that the unique features of this new *Coleus* are stable and reproduced true to type in successive generations.

SUMMARY OF THE INVENTION

Plants of the cultivar Kagegawa CE8 have not been observed under all possible environmental conditions. The phenotype may vary somewhat with variations in environment such as temperature and light intensity without, however, any variance in genotype.

The following traits have been repeatedly observed and are determined to be the unique characteristics of 'Kakegawa CE8'. These characteristics in combination distinguish 'Kakegawa CE8' as a new and distinct *Coleus* cultivar:

1. Low and outwardly spreading plant habit.
2. Freely branching and vigorous growth habit.
3. Strong lateral branches.
4. Green and dark purple bi-colored leaves with dark purple-colored venation and green and purple-colored petioles.

Plants of the new *Coleus* are most similar to plants of the parent selection. Plants of the new *Coleus* differ primarily from plants of the parent selection in foliage coloration.

Plants of the new *Coleus* can also be compared to plants of the *Coleus* cultivar Salamander, not patented. In side-by-side comparisons conducted in Cartago, Costa Rica, plants of the new *Coleus* differed from plants of the cultivar Salamander in the following characteristics:

1. Plants of the new *Coleus* are more compact than plants of the cultivar Salamander.
2. Plants of the new *Coleus* are more freely branching than plants of the cultivar Salamander.
3. Plants of the new *Coleus* are more outwardly spreading in plant habit than plants of the cultivar Salamander.

Plants of the new *Coleus* can also be compared to plants of the *Coleus* cultivars Kakegawa CE1, disclosed in U.S. Plant patent application Ser. No. 10/753,810; Kakegawa CE2, disclosed in U.S. Plant patent application Ser. No. 10/753,809; Kakegawa CE3, disclosed in U.S. Plant patent application Ser. No. 10/753,808; and Kakegawa CE5, disclosed in a U.S. Plant patent application filed concurrently. However, in side-by-side comparisons conducted in Salinas, Calif., plants of the new *Coleus* differed primarily from plants of the cultivars Kakegawa CE1 and Kakegawa CE2 in plant and leaf size and from plants of the cultivars Kakegawa CE3 and Kakegawa CE5 primarily in foliage coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Coleus*.

The photograph at the top of the sheet comprises a side perspective view of typical plant of 'Kakegawa CE8' grown in a container.

The photograph at the bottom of the sheet comprises a close-up view of typical leaves of 'Kakegawa CE8'.

DETAILED BOTANICAL DESCRIPTION

The cultivar Kakegawa CE8 has not been observed under all possible environmental conditions. The phenotype may vary somewhat with variations in environment such as temperature and light intensity without, however, any variance in genotype.

The aforementioned photographs, following observations and measurements describe plants grown during the winter and spring in Salinas, Calif., in a glass-covered greenhouse and under conditions which approximate commercial production cultural and environmental conditions. Plants were about ten weeks from rooted cuttings and were grown in 10-cm containers. During the production of the plants, day temperatures were about 24° C., night temperatures were about 16° C. and light levels ranged from 4,000 to 6,000 footcandles.

In the following description, color references are made to The Royal Horticultural Society Colour Chart, 1995 Edition, except where general terms of ordinary dictionary significance are used.

Botanical classification: *Coleus×hybridus* cultivar Kakegawa CE8.

Parentage: Seedling from a self-pollination of a proprietary selection of *Coleus×hybridus* identified as code number 9CL-1, not patented.

Propagation:

*Type cutting.*—Terminal cuttings.

*Time to initiate roots.*—About four days at 24° C.

*Time to develop roots.*—About ten days at 24° C.

*Root description.*—Fine, fibrous, white in color.

*Rooting habit.*—Freely branching.

Plant description:

*Form.*—Annual potted or garden plant; low and outwardly spreading plant habit. Rapid growth rate; vigorous.

*Plant height.*—About 13 cm.

*Plant diameter.*—About 36 cm.

*Branching habit.*—Freely branching with about nine lateral branches per plant.

*Lateral branches.*—Length: About 22 cm. Diameter: About 7 mm. Internode length: About 3.5 cm. Strength: Strong. Aspect: Initially upright then outwardly spreading. Shape, in cross-section: Squarish. Texture: Pubescent. Color: 147C tinged with 183D.

*Foliage description.*—Arrangement: Opposite; simple. Length: About 4 cm. Width: About 5 cm. Shape: Broadly deltoid. Apex: Broadly acute to nearly rounded. Base: Truncate. Margin: Deeply crenate; scalloped. Texture, upper and lower surfaces: Pubescent. Venation pattern: Pinnate; netted. Color: Developing foliage, upper surface: Towards the margins and base, 147A; center and venation, 187A. Developing foliage, lower surface: 147C; venation, 147C to 147D. Fully expanded foliage, upper surface: Towards the margins and base, 147A; center and venation, darker than 187A. Fully expanded foliage, lower surface: 147C; random speckles, 187A; venation, 147C to 147D. Petiole length: About 2.3 cm. Petiole diameter: About 2 mm. Petiole color: 146B tinged with 183B.

Flower description: Flower development has not been observed.

Disease/pest resistance: Plants of the new *Coleus* have not been noted to be resistant to pathogens or pests common to *Coleus*.

Temperature tolerance: Plants of the new *Coleus* have been observed to tolerate temperatures from 2 to 35° C.

It is claimed:

1. A new and distinct cultivar of *Coleus* plant named 'Kakegawa CE8', as illustrated and described.

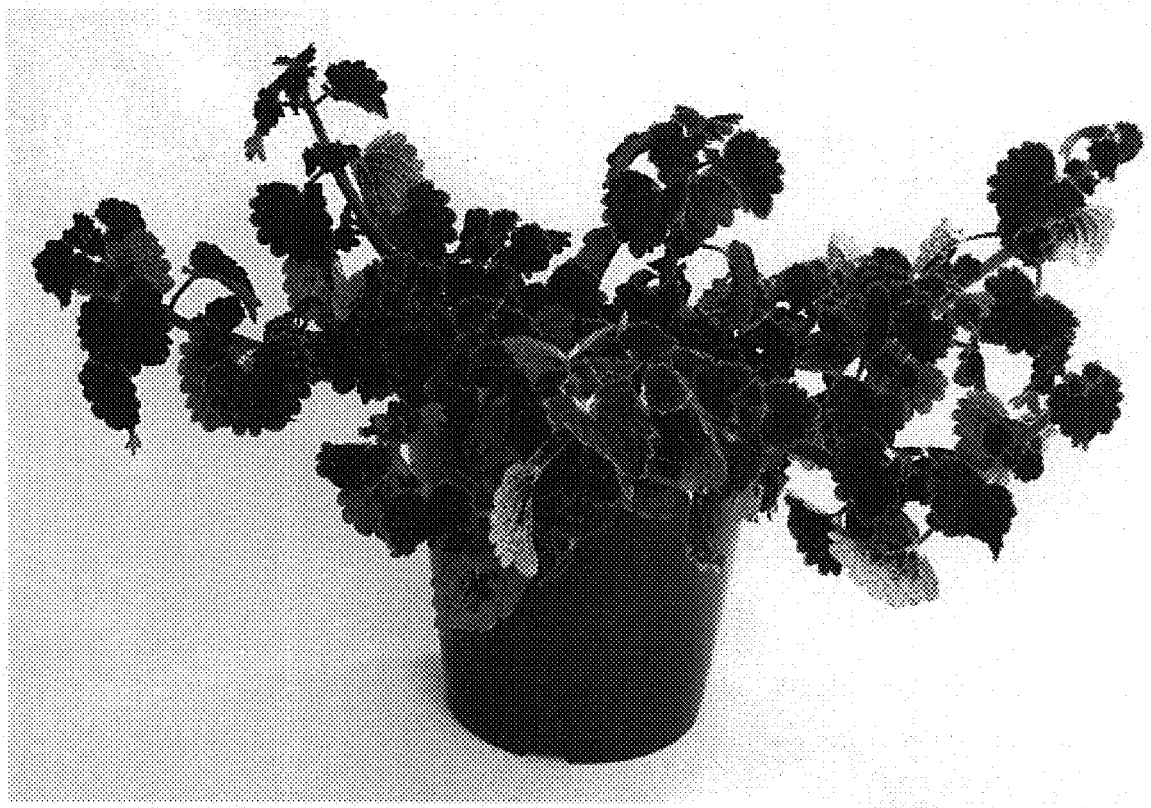
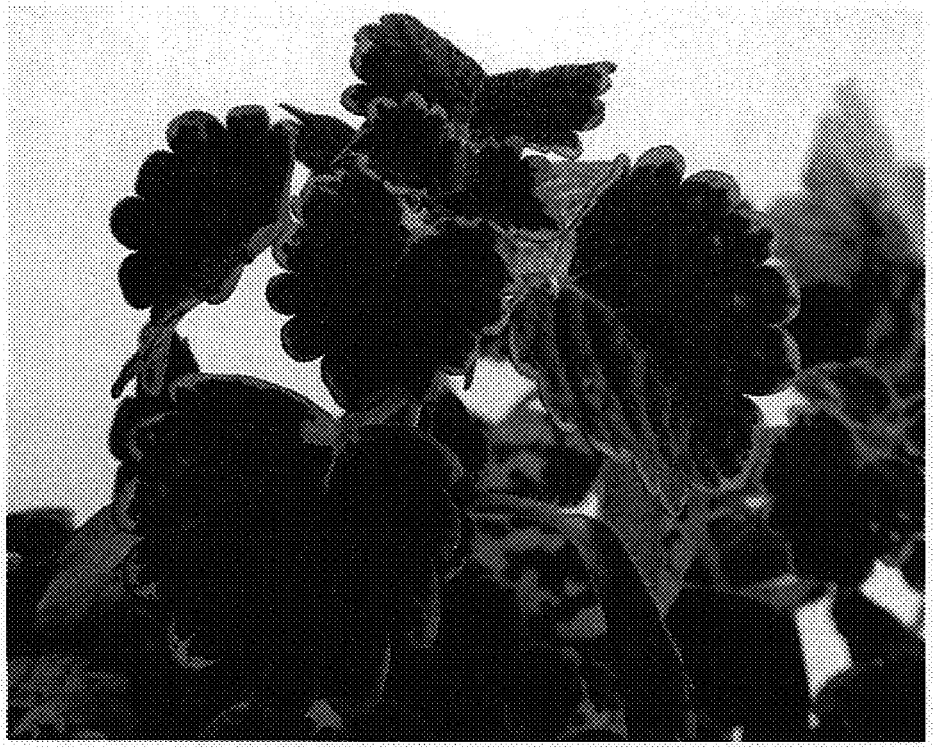

* * * * *